(12) United States Patent
Fuchs et al.

(10) Patent No.: US 9,173,870 B2
(45) Date of Patent: *Nov. 3, 2015

(54) TOPICAL LOCALIZED ISOXAZOLINE FORMULATION

(75) Inventors: Stefan Fuchs, Schwabenheim (DE); Anja Regina Heckeroth, Stadecken-Elsheim (DE); Ramona Müller, Eich (DE); Heike Williams, Schwabenheim (DE); Hartmut Zoller, Hochheim (DE)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/996,263

(22) PCT Filed: Dec. 22, 2011

(86) PCT No.: PCT/EP2011/073828
§ 371 (c)(1),
(2), (4) Date: Jun. 20, 2013

(87) PCT Pub. No.: WO2012/089622
PCT Pub. Date: Jul. 5, 2012

(65) Prior Publication Data
US 2013/0281501 A1   Oct. 24, 2013

Related U.S. Application Data

(60) Provisional application No. 61/430,240, filed on Jan. 6, 2011.

(51) Int. Cl.
*A01N 43/80* (2006.01)
*A61K 31/42* (2006.01)
*A61K 45/06* (2006.01)

(52) U.S. Cl.
CPC ............... *A61K 31/42* (2013.01); *A01N 43/80* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2004/0116419 A1 | 6/2004 | Heaney et al. | |
| 2007/0020304 A1* | 1/2007 | Tamarkin et al. | ............. 424/405 |
| 2007/0066617 A1 | 3/2007 | Mita et al. | |
| 2011/0059988 A1* | 3/2011 | Heckeroth et al. | ....... 514/255.05 |

FOREIGN PATENT DOCUMENTS

| | | | |
|---|---|---|---|
| WO | 2006/042099 A1 | 4/2006 | |
| WO | 2007/079162 A1 | 7/2007 | |
| WO | 2009/002809 A2 | 12/2008 | |
| WO | 2009/003075 A1 | 12/2008 | |
| WO | 2009/024541 A2 | 2/2009 | |
| WO | 2010/070068 A2 | 6/2010 | |
| WO | WO 2010070068 A2 * | 6/2010 | ........... C07D 413/04 |
| WO | 2010/079077 A1 | 7/2010 | |
| WO | 2011/075591 A1 | 6/2011 | |
| WO | 2011/124998 A1 | 10/2011 | |

OTHER PUBLICATIONS

Ozoe et al. (Biochemical and Biophysical Research Communications, Nov. 29, 2009, 391, 744-749).*
Kumar et al., "Comparative activity of three repellents against the ticks Rhipicephalus sanguineus and Argas persicus", Medical and Veterinary Entomology, 1992, pp. 47-50, vol. 6.
European Search Report for EP Application No. 10 19 7089, dated May 27, 2011.
International Search Report for corresponding PCT/EP2011/073828, mailed on Sep. 5, 2012.

* cited by examiner

*Primary Examiner* — Dennis Heyer
*Assistant Examiner* — Daniel M Podgorski

(57) ABSTRACT

This invention provides topical localized formulations comprising an isoxazoline compound and a pharmaceutically or veterinary acceptable liquid carrier vehicle comprising N,N-diethyl-3-methylbenzamide as a solvent and an improved method for controlling, and preventing parasite infestation in animals.

4 Claims, 4 Drawing Sheets

Figure 1: Plasma concentration in Beagle dogs
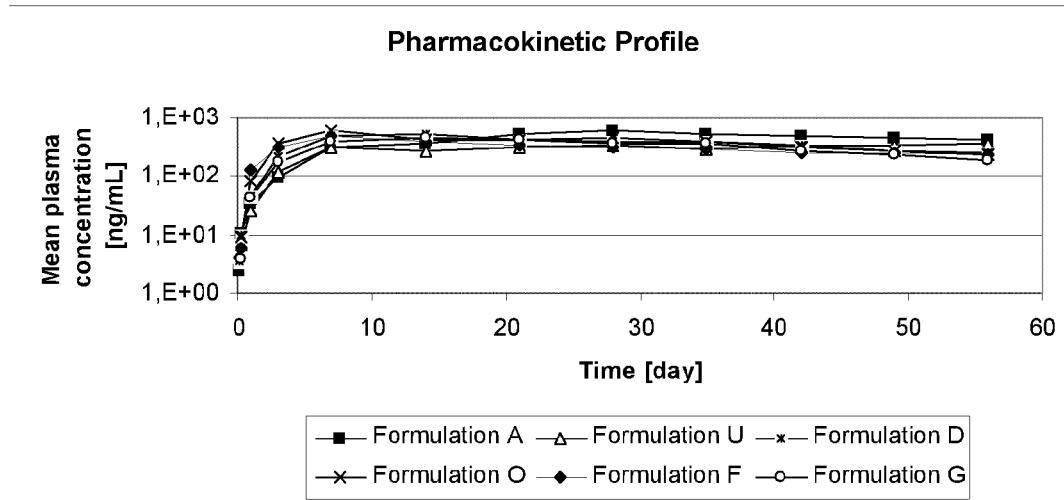
Figure 2: Plasma concentration in Beagle dogs
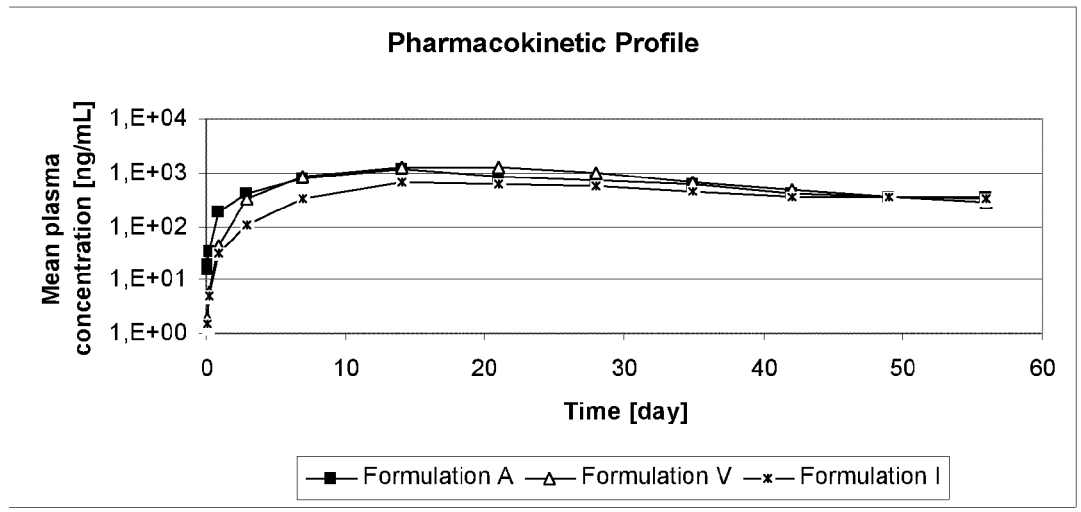

Figure 3: Plasma concentration in Beagle dogs
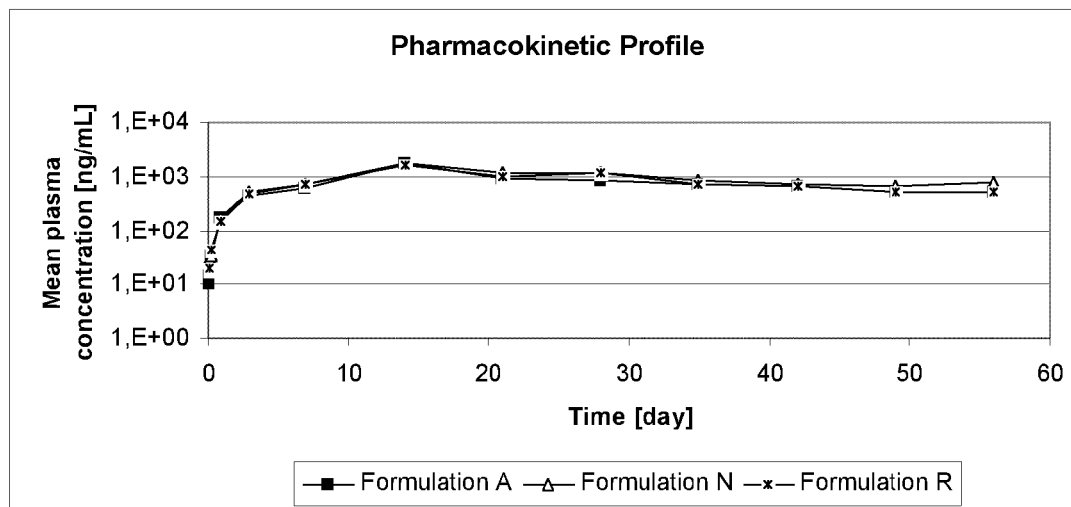
Figure 4: Plasma concentration in Beagle dogs
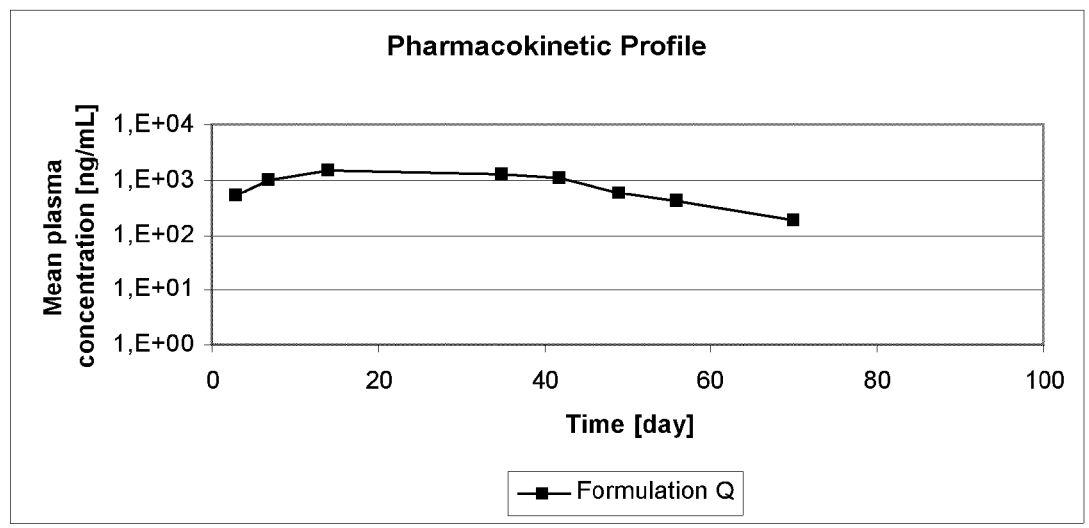

Figure 5: Plasma concentration in Beagle dogs
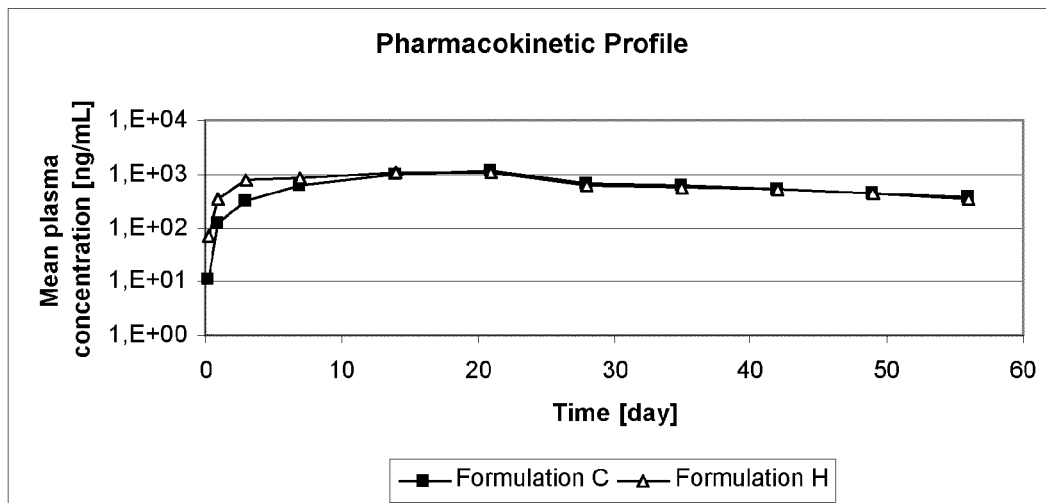
Figure 6: Plasma concentration in Beagle dogs
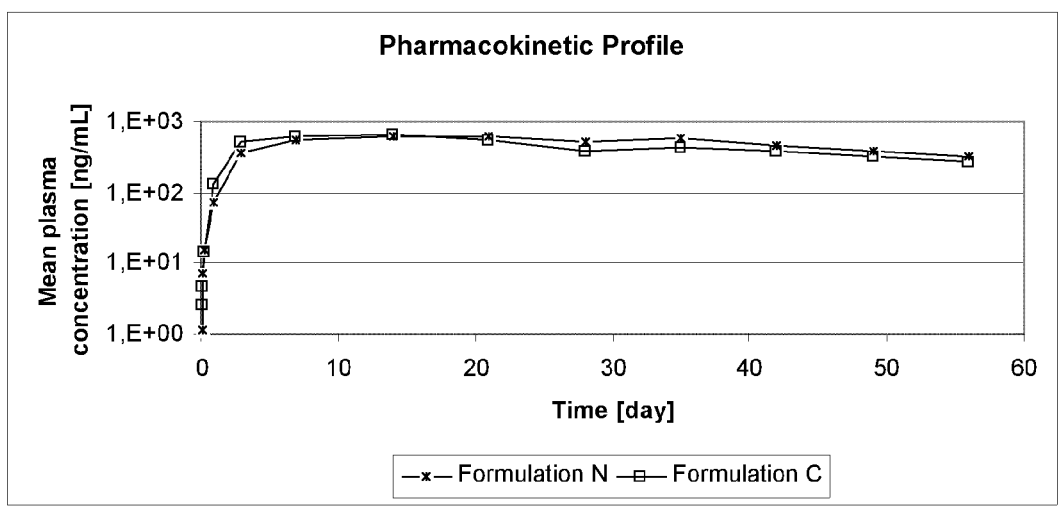

Figure 7: Isoxazoline compound and moxidectin plasma concentration in Beagle dogs (Formulation N)
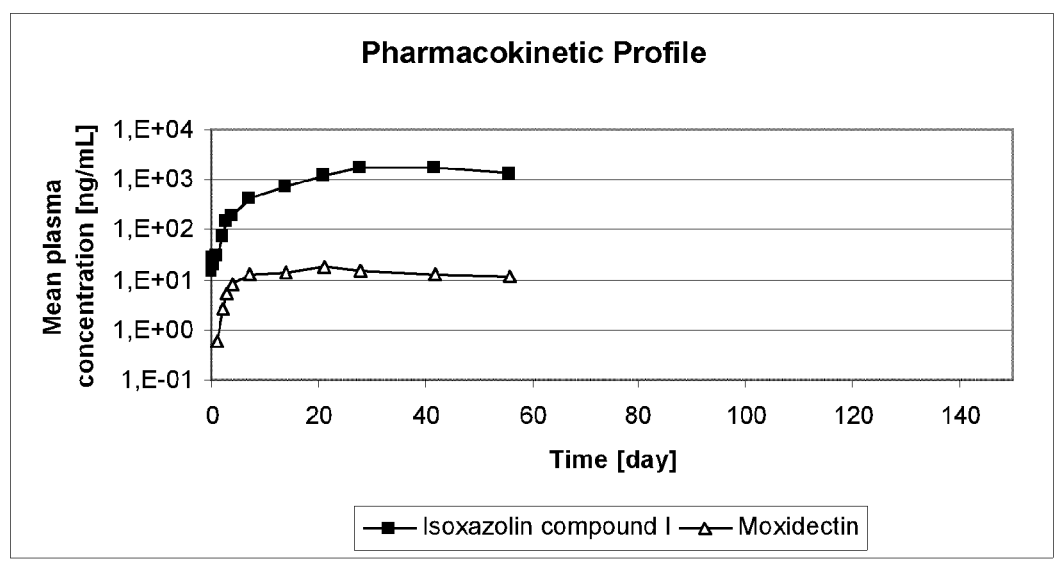

TOPICAL LOCALIZED ISOXAZOLINE FORMULATION

CROSS-REFERENCE TO RELATED APPLICATIONS

This application is a national stage entry under 35 U.S.C. §371 of PCT/EP2011/073828, filed on Dec. 21, 2011, which claims priority to U.S. Provisional Application No. 61/430,240, filed on Jan. 6, 2011; and EP Application No. 10197089.5, filed on Dec. 27, 2010. The content of PCT/EP2011/073828 is hereby incorporated by reference in its entirety.

FIELD OF THE INVENTION

This invention provides topical localized formulations comprising an isoxazoline compound and a pharmaceutically or veterinary acceptable liquid carrier vehicle. This invention also provides for an improved method for controlling, and preventing parasite infestation in animals.

BACKGROUND OF THE INVENTION

A number of pests and parasites can infest or infect domestic animals such as cattle, horses, pigs, sheep and also companion animals such as cats and dogs. These pests and parasites are of great nuisance to both the animals and their owners.

Ectoparasites such as ticks, mites, lice, flies and fleas irritate the animals and can cause disease, either by themselves, or by carrying vector transmitted pathogens.

New economic methods and compositions for the prevention, treatment and control of parasites in warm-blooded animals are constantly being sought.

A new family of insecticide isoxazoline compounds has been described in various patent applications; for example, in US patent application US 2007/0066617, and International Patent applications WO 2007/079162, WO 2009/002809, WO 2009/024541, WO 2009/003075, WO 2010/070068, WO 2010/079077, WO 2011/075591 and WO 2011/124998.

As these isoxazoline compounds have been originally investigated for their use in the agricultural area it is necessary to identify specific formulations that allow their veterinary use, i.e. safe administration to control parasites in animals effectively.

One known and convenient way of administering an ecto-parasiticide compound to an animal is the topical localized administration, e.g. as spot-on or pour-on.

However, prior art formulations and conventional topical localized ectoparasiticide formulations that use suggested solvents for isoxazoline compounds have difficulties applying effective amounts of isoxazoline compounds with acceptable cosmetic appearance. Particularly, high volumes of conventional topical localized formulations can result in product run-off and sodden appearances of the fur after administration and high concentration formulations can result in insolubility (crystallization) of the active ingredient, skin irritation as well as undesirable product characteristics, such as poor viscosity, insufficient spreading, poor evaporation and inadequate permeation.

Thus, what is needed in the art, are topical localized formulations of isoxazoline compounds, which avoid the drawbacks mentioned above.

SUMMARY OF THE INVENTION

The current invention provides topical localized formulations for the administration of isoxazoline compounds that overcome the drawbacks of the prior art. The formulations of the invention deliver effective amounts of isoxazoline compounds after topical localized administration and with acceptable cosmetic appearance.

In one aspect the current invention is directed to a topical localized formulation for the treatment or prophylaxis of parasite infestation in animals which comprises an effective amount of at least one isoxazoline compound of the Formula (I)

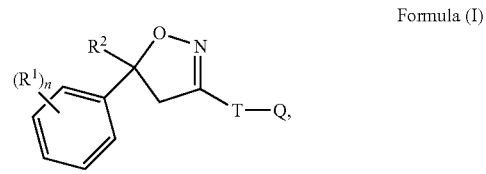

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain, especially a three or four membered chain;
Q=X—$NR^3R^4$ or a 5-membered N-heteroaryl ring, which is optionally substituted by one or more radicals;
X=$CH_2$, $CH(CH_3)$, $CH(CN)$, CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

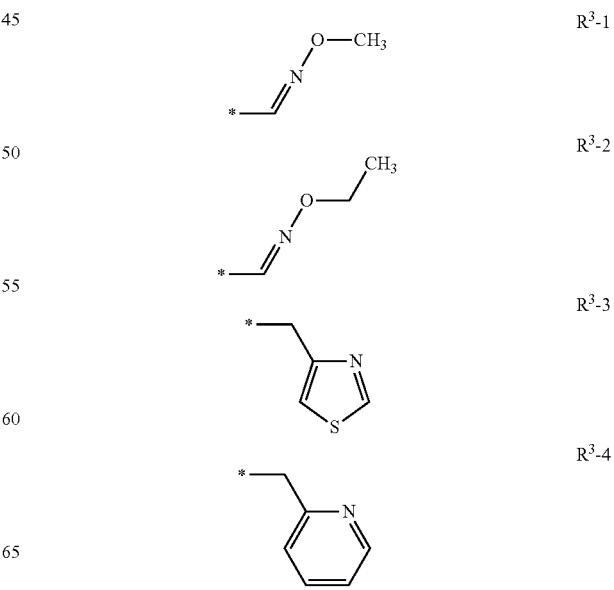

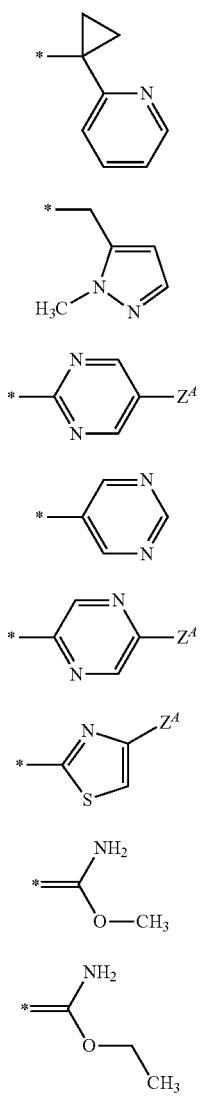

wherein $Z^A$=hydrogen, halogen, cyano, halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

Or $R^3$ and $R^4$ together form a substituent selected from the group consisting of:

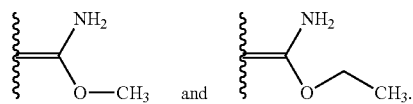

and a veterinary acceptable liquid carrier vehicle wherein the liquid carrier vehicle comprises N,N-diethyl-3-methylbenzamide as a solvent.

In one embodiment the liquid carrier vehicle comprises N,N-diethyl-3-methylbenzamide as sole solvent. In another embodiment at least one additional veterinary acceptable co-solvent is present.

In one embodiment the composition comprises additionally an effective amount of a macrocyclic lactone compound selected from ivermectin, moxidectin, milbemycin oxime, selamectin, emamectin, latidectin and lepimectin or a salt thereof and/or an insect growth regulator compound selected from fenoxycarb, lufenuron, diflubenzuron, novaluron, triflumuron, fluazuron, cyromazine, methoprene and pyriproxyfen.

Another aspect of the current invention is a method for treatment or prophylaxis of parasite infestation of an animal comprising spot-on or pour-on administration of a localized topical formulation of claim 1.

These and other embodiments are disclosed or are obvious from and encompassed by the following Detailed Description.

BRIEF DESCRIPTION OF THE DRAWINGS

FIG. 1: Plasma concentration of Compound A after spot-on administration of formulations A, U, D, O, F and G to Beagle dogs FIG. 2: Plasma concentration of Compound A after spot-on administration of formulations A, V and I to Beagle dogs FIG. 3: Plasma concentration of Compound A after spot-on administration of formulations A, N and R to Beagle dogs FIG. 4: Plasma concentration of Compound A after spot-on administration of formulation Q to Beagle dogs FIG. 5: Plasma concentration of Compound A after spot-on administration of formulations C and H to Beagle dogs FIG. 6 Plasma concentration of Compound A after spot-on administration of formulations N and C to Beagle dogs FIG. 7 Compound A and moxidectin plasma concentration after spot-on administration of formulation G to Beagle dogs

DETAILED DESCRIPTION OF THE INVENTION

The topical localized formulation according to the invention comprises an isoxazoline compound of the Formula (I)

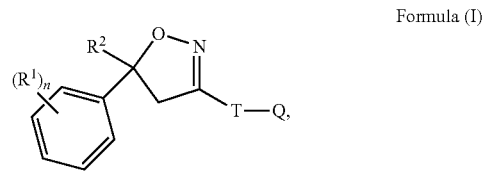

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain CH—CH=CH—CH, N—CH=CH—CH, CH—N=CH—CH, CH—CH=N—CH, or CH—CH=CH—N, HC=HC—CH, CH—CH=CH, CH=CH—N, N—CH=CH;
Q=X—$NR^3R^4$ or a 5-membered N-heteroaryl ring, which is optionally substituted by one or more radicals $Z^A$, $Z^B$ $Z^D$;
X=$CH_2$, $CH(CH_3)$, CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

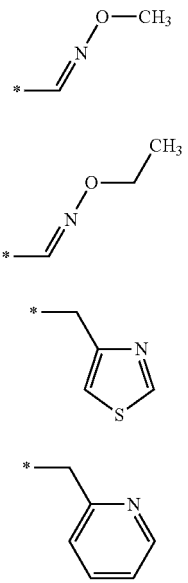

R³-1
R³-2
R³-3
R³-4
R³-5
R³-6
R³-7
R³-8
R³-9
R³-10

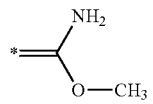

R³-11

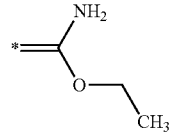

R³-12

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or $R^3$ and $R^4$ together form a substituent selected from the group consisting of:

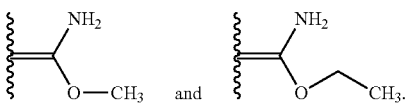

wherein $Z^A$=hydrogen, halogen, cyano, halomethyl ($CF_3$);

and a veterinary acceptable liquid carrier vehicle wherein the liquid carrier vehicle comprises N,N-diethyl-3-methylbenzamide as a solvent.

In one preferred embodiment in Formula (I) T is selected from

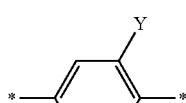

T-1

T-2

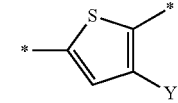

T-3

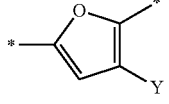

T-4

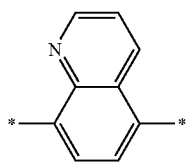 T-5
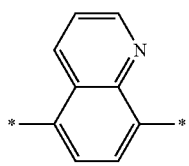 T-6
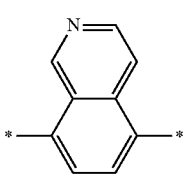 T-7
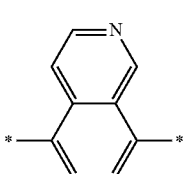 T-8
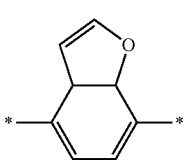 T-9
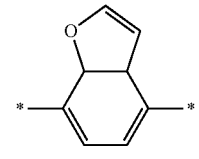 T-10
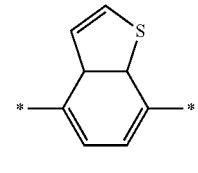 T-11
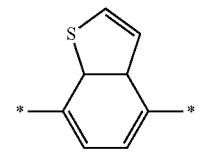 T-12
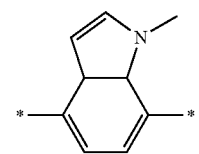 T-13
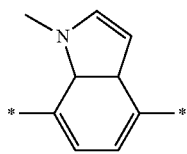 T-14
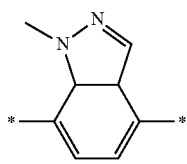 T-15
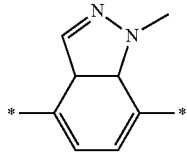 T-16
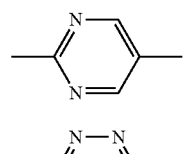 T-17
T-18
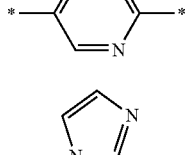 T-19
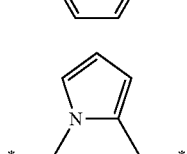 T-20
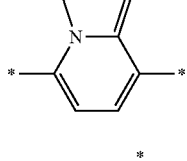 T-21
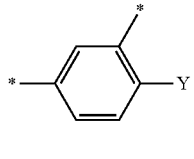 T-22
wherein in T-1, T-3 and T-4 the radical Y is hydrogen, halogen, methyl, halomethyl, ethyl, haloethyl.
In an preferred embodiment in Formula (I) Q is selected from
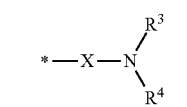 Q-1

-continued
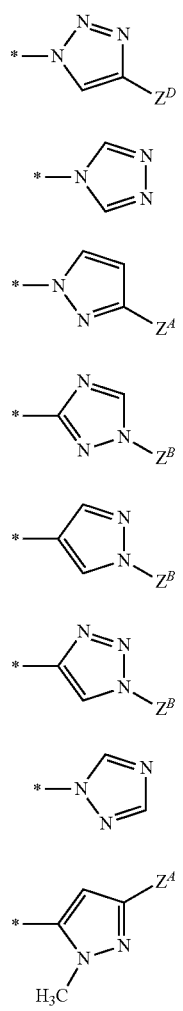
Wherein $R^3$, $R^4$, X and $Z^A$ are as defined above.
$Z^B =$
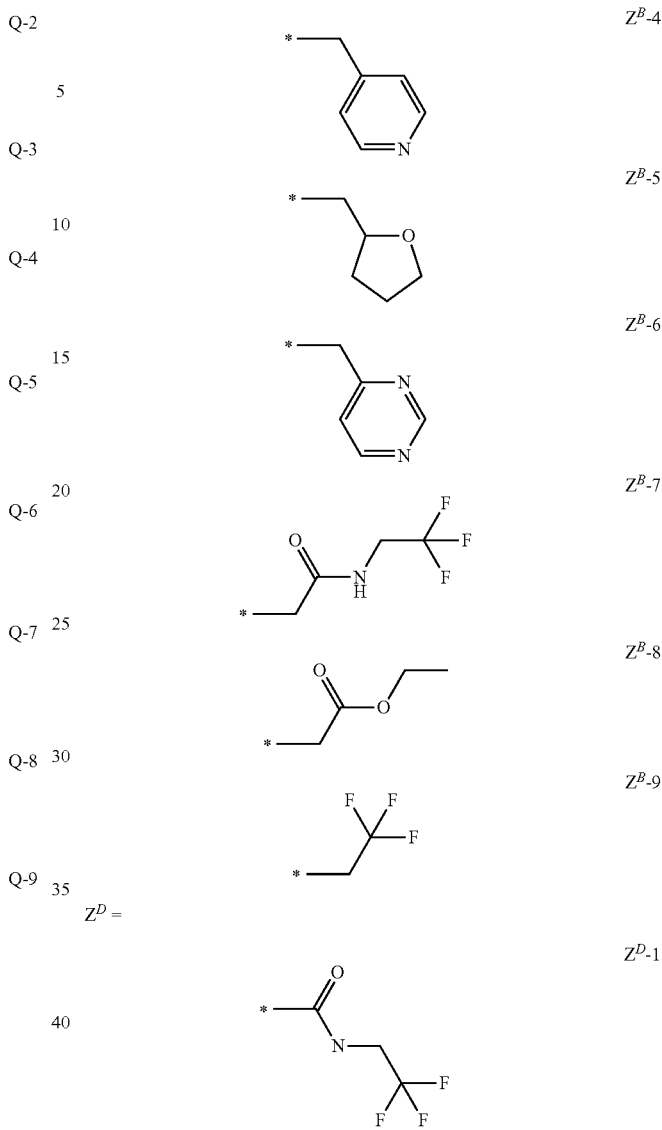
-continued
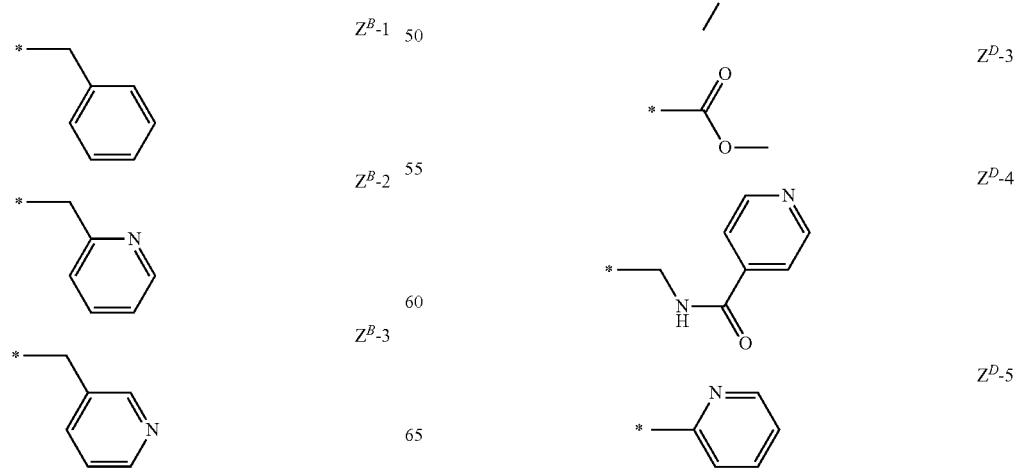

-continued

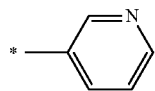

$Z^D$-6

5

Preferred compounds of Formula (I) are:

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-Cl, 5Cl | $CF_3$ | $CH_2C(O)NHCH_2CH_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CH_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CH_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | | T-2 | — | Q-7 | $Z^B$-7 | |
| 3-Cl, 5Cl | $CF_3$ | — | | T-2 | — | Q-5 | $Z^B$-7 | |
| 3-Cl, 5Cl | $CF_3$ | — | | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-Cl, 5Cl | $CF_3$ | $CH_2C(O)NHCH_2CC$ | H | T-3 | $CH_3$ | Q-1 | — | C(O) |
| 3-Cl, 5Cl | $CF_3$ | $CH_2C(O)NHCH_2CN$ | H | T-3 | $CH_3$ | Q-1 | — | C(O) |
| 3-Cl, 5Cl | $CF_3$ | $CH_2C(O)NHCH_2CH_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CH_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CH_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CH_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-Cl, 5-Cl | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CH_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |
| 3-$CF_3$, 5-$CF_3$ | $CF_3$ | $CH_2C(O)NHCH_2CH_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CH_3$ | H | T-21 | — | Q-1 | — | C(O) |
| 3-Cl, 5-Cl | $CF_3$ | $CH_2CH_2SCH_3$ | H | T-21 | — | Q-1 | — | C(O) |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $CH_2C(O)NHCH_2CH_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

Especially preferred compounds of Formula (I) are

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | — | T-2 | — | Q-5 | $Z^B$-7 | |
| 3-Cl, 5Cl | $CF_3$ | — | — | T-2 | — | Q-2 | $Z^D$-1 | |

-continued

| (R¹)ₙ | R² | R³ | R⁴ | T | Y | Q | Z | X |
|---|---|---|---|---|---|---|---|---|
| 3-Cl, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CC | H | T-3 | CH₃ | Q-1 | — | C(O) |
| 3-Cl, 5-Cl | CF₃ | CH₂C(O)NHCH₂CN | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

A more preferred compound has the formula (II),

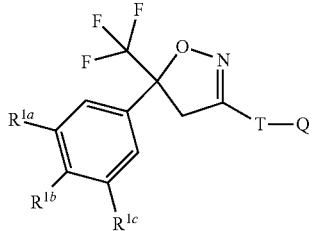

Formula II wherein
$R^{1a}, R^{1b}, R^{1c}$ are independently from each other hydrogen, Cl or CF₃, preferably $R^{1a}$ and $R^{1c}$ are Cl and $R^{1b}$ is hydrogen,
T is

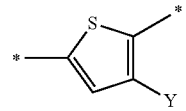

T-1

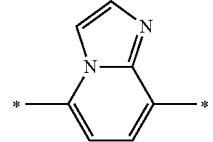

T-2

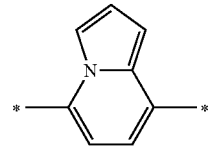

T-3

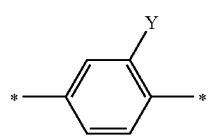

T-20

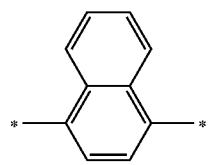

T-21 wherein Y is methyl, bromine, Cl, F, CN or C(S)NH₂,
Q is as described above.

In another preferred embodiment in $R^3$ is H and $R^4$ is —CH₂—C(O)—NH—CH₂—CF₃, —CH₂—C(O)—NH—CH₂—CH₃, —CH₂—CH₂—CF₃ or —CH₂—CF₃

In one embodiment the compound of formula (I) is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN [864731-61-3]).

In another embodiment the compound of formula (I) is (Z)-4-[5-(3,5-Dichlorophenyl)-5-trifluoromethyl-4,5-dihydroisoxazol-3-yl]-N-[(methoxyimino)methyl]-2-methylbenzamide (CAS RN [928789-76-8]).

An especially preferred compound is

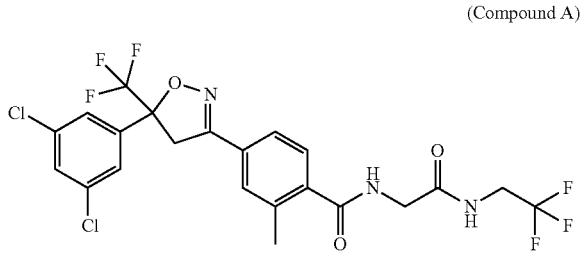 [SMILES: Cc1cc(C2=NOC(c3cc(Cl)cc(Cl)c3)(C(F)(F)F)C2)ccc1C(=O)NCC(=O)NCC(F)(F)F]

(Compound A)

Especially preferred compounds of Formula (II) are:

| (R¹)ₙ | R² | R³ | R⁴ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-Cl, 5Cl | CF₃ | — | | T-2 | — | Q-6 | $Z^B$-7 | |
| 3-Cl, 5Cl | CF₃ | — | — | T-2 | — | Q-7 | $Z^B$-7 | |
| 3-Cl, 5Cl | CF₃ | — | — | T-2 | — | Q-5 | $Z^B$-7 | |
| 3-Cl, 5Cl | CF₃ | — | — | T-2 | — | Q-2 | $Z^D$-1 | |
| 3-Cl, 5Cl | CF₃ | CH₂C(O)NHCH₂CF₃ | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

Isoxazoline compounds are known in the art and these compounds and their use as parasiticide are described, for example, in US patent application No. US 2007/0066617, and International Patent applications WO 2007/079162, WO 2009/002809, WO 2009/024541, WO 2009/003075, WO 2010/070068, WO 2010/079077, WO 2011/075591 and WO 2011/124998, the disclosures of which, as well as the references cited herein, are incorporated by reference. This class of compounds is known to possess excellent activity against ectoparasites such as ticks and fleas.

The isoxazoline compounds may exist in various isomeric forms. A reference to an isoxazoline compound always includes all possible isomeric forms of such compound. Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Isoxazoline compounds of formula (I) can be prepared according to one or other of the processes described e.g. in Patent Applications US 2007/0066617, WO 2007/079162, WO 2009/002809, WO 2010/070068 and WO 2010/079077, 2011/075591 and WO 2011/124998 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

The formulations according to the invention are effective for long durations of time in the treatment of ectoparasites of mammals and, in particular, of fleas and ticks in small mammals such as dogs and cats. Advantageously, the formulations of the invention retain the desired physical characteristics over time, without loss of potency of the active. Further, the formulations of the invention exhibit sufficient viscosity, which allows for the retention of said composition when administered topically to an animal's skin or hair.

Furthermore the formulations of the current invention have favorable product characteristics i.e. they are stable and are cosmetically acceptable.

Cosmetic acceptability includes the (absence of) smell of hair and skin, wetness of the hair and skin of the application site, the overall appearance of the dogs' coat, particularly signs such as dryness, wiry look, brittleness, dullness, hair loss and the appearance of residue of the hair in the proximity of the administration site.

Such cosmetic acceptability is very important for products for topical localized administration to companion animals like dogs and cats, because the pet owner would not accept long lasting changes in the appearance of the fur of their pet following the administration.

With the formulations according to the current invention it was possible to identify topical localized formulations that allow the administration of isoxazoline compounds for a long acting efficacy against ticks and fleas while being cosmetically acceptable.

Topical localized formulations are understood to refer to a ready-to-use formulation in form of a spot-on, pour-on or spray-on formulation. The expression spot-on or pour-on method is understood to refer to a ready-to-use concentrate intended to be applied topically and locally on the animal. This sort of formulation is intended to be applied directly to a relatively small area of the animal, preferably on the animal's back and breech or at one or several points along the line of the back and breech.

Spot-on administration is a topical localized administration of a concentrated solution, suspension, microemulsion or emulsion for intermittent application to a spot on the animal, generally between the two shoulders in 1, 2, 3, 4, or 5 locations (spots), if more than one spot preferably down the back of the animal. Alternatively the product is administered by administering a line.

The pour-on formulation is typically applied by pouring in one or several lines or in a spot-on along the dorsal midline (back) or shoulder of an animal. More typically, the formulation is applied by pouring it along the back of the animal, following the spine. A pour-on formulation is more common for control of parasites in livestock animals, such as e.g. cattle, pigs, sheep and horses. The pour-on formulations of this invention can be in the form of a liquid, emulsion, foam, paste, aerosol, ointment, salve or gel. Typically, the pour-on formulation is liquid.

The formulation can also be applied to the animal by other conventional methods, including wiping an impregnated material over at least a small area of the animal, or applying it using a commercially available applicator, by means of a syringe, by spraying or by using a spray race.

A pour-on or spot-on formulation generally can advantageously comprise the isoxazoline compound of formula (I) in a proportion of about 0.01 to about 70%, of about 1 to about 50%, 10 to 40%, 20 to 35%, 25 to 30% about 20%, 25%, 28%, 30%, 33%, 50%, (percentages as weight by volume=W/V).

The topical localized formulation allows or facilitates the isoxazoline compound to penetrate the skin and act on other body parts (e.g., the entire body). Such a pour-on or spot-on formulation can be prepared by dissolving, suspending, or emulsifying the isoxazoline in a suitable veterinarily acceptable carrier.

In one embodiment the topical localized formulation comprises a carrier comprising N,N-diethyl-3-methylbenzamide (DEET, previously called N,N-diethyl-meta-toluamide or N,N-Diethyl-m-toluamide) as a sole solvent. In one embodiment at least one additional veterinary acceptable co-solvent is present. N,N-diethyl-3-methylbenzamide is a well known chemical compound which has long been used as an insect repellant. Various syntheses for the preparation thereof are well-known to the art.

A pour-on or spot-on formulation generally can advantageously comprise the N,N-diethyl-3-methylbenzamide in a proportion of about 1 to about 50%, preferably of about 5 to about 37%, 8 to 28%, 10 to 23%, 15 to 20% about 5%, 7%, 9%, 10%, 11%, 14%, 15%, 17%, 18%, 20%, 23%, 28%, 33%, 37%, 44% (percentages as weight by volume=W/V).

The co-solvent for the liquid carrier includes pharmaceutically acceptable solvents known in the formulation art.

These solvents include, for example, acetone dichloromethane, glycofurol, acetonitrile, n-butyl ether, monomethylacetamide, dipropylene glycol monomethyl ether, diethyl phthalate fatty acid esters, such as the diethyl ester or diisobutyl adipate, water, alkanol, benzyl benzoate, dipropylene glycol monomethyl ether, diethylene glycol monobutyl ether, silicone, dimethylacetamide, 2,2-dimethyl-4-oxy-methylene-1,3-dioxolane. N,N-dimethylalkanamides (e.g. N,N dimethylformamide), limonene, eucalyptol, dimethyl sulfoxide, -alkylpyrrolidones (e.g. N-methylpyrrolidone, 2-pyrrolidone), liquid polyoxyethylene glycols, methylene glycol, ethylene glycol, propylene glycol, dipropylene glycol, polypropylene glycol, butyl diglycol, dipropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as methyl ethyl ketone, cyclohexanone, 2-heptanone, isophorone and 4-hydroxy-4-methyl-2-pentanone, acetates such as ethyl acetate, benzyl acetate, isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as phenyl ethyl alcohol, methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol.

Such solvents also include glycerol esters of saturated and unsaturated fatty acids (typically $C_6$-$C_{22}$), such as plant seed and fruit oils (e.g. oils of olive, castor, linseed, sesame, corn (maize), peanut, sunflower, grapeseed, safflower, cottonseed, soybean, rapeseed, coconut and palm kern and mixtures thereof, e.g. polyethoxylated castor oil. Such solvents also include alkylated fatty acids (e.g., methylated, ethylated, butylated) wherein the fatty acids may be obtained by hydrolysis of glycerol esters from plant and animal sources, and can be purified by distillation.

In one embodiment the solvent is N,N-diethyl-3-methylbenzamide; and the co-solvent is selected from the group consisting of acetone, acetonitrile, benzyl alcohol, butyl diglycol, dimethylacetamide, dimethylsulfoxide, dimethylformamide, dipropylene glycol n-butyl ether, ethyl alcohol, isopropanol, methanol, phenylethyl alcohol, isopropanol, ethylene glycol monoethyl ether, ethylene glycol monomethyl ether, monomethylaceamide, dipropylene glycol monomethyl ether, liquid polyoxyethylene glycols, propylene glycol, N-methylpyrrolidone, 2-pyrrolidone, limonene, eucalyptol, diethylene glycol monoethyl ether, ethylene glycol, diethyl phthalate, polyethoxylated castor oil, methyl ethyl ketone, glycofurol, ethyl-L-lactate, and a mixture of at least two of these co-solvents.

In another embodiment the co-solvent is selected from the group consisting of dimethyl sulfoxide, acetone, dimethylacetamide, ethyl alcohol, dipropylene glycol monomethyl ether, methylethyl ketone, glycofurol, ethyl-L-lactate, and a mixture of at least two of these cosolvents.

In one embodiment the liquid carrier vehicle comprises N,N-diethyl-3-methylbenzamide as solvent and a organic co-solvent is selected from acetone, ethyl-L-lactate, dimethyl sulfoxide, dimethylacetamide and glycofurol.

In another embodiment the organic solvent in the local topical formulation is N,N-diethyl-3-methylbenzamide and the organic co-solvent is a mixture of at least two of acetone, ethyl-L-lactate, dimethyl sulfoxide, dimethylacetamide and glycofurol.

The co-solvent can advantageously be present in the composition according to a volume/volume (V/V) ratio with respect to N,N-diethyl-3-methylbenzamide of between about 4/1 and about 1/5.

A pour-on or spot-on formulation generally can advantageously comprise acetone in a proportion of about 0 to about 50%, preferably of about 5 to about 35%, about 5%, 10%, 15%, 20%, 25%, 30%, 35%, (percentages as volume by volume=V/V).

A pour-on or spot-on formulation generally can advantageously comprise dimethylacetamide in a proportion of about 0 to about 60%, preferably of about 5 to about 50%, about 5%, 10%, 15%, 20%, 25%, 30%, 35%, 40%, 45%, 50% (percentages as volume by volume=V/V).

A pour-on or spot-on formulation generally can advantageously comprise dimethylsulfoxide in a proportion of about 0 to about 50%, preferably of about 5 to about 35%, about 5%, 10%, 15%, 20%, 25%, 30%, 35%, (percentages as volume by volume).

A pour-on or spot-on formulation generally can advantageously comprise N-methylpyrrolidone in a proportion of about 0 to about 50%, preferably of about 5 to about 35%, about 5%, 10%, 15%, 20%, 25%, 30%, 35% (percentages as volume by volume).

A pour-on or spot-on formulation generally can advantageously comprise methylethylketone in a proportion of about 0 to about 50%, preferably of about 5 to about 40%, about 5%, 10%, 15%, 20%, 25%, 30%, 35%, 40% (percentages as volume by volume).

The topical localized formulation can also include one or more additional ingredients. Examples of suitable additional ingredients are penetration enhancers, spreading agents, stabilizers such as antioxidants/preservatives, adhesion promoters and viscosity modifiers, crystallization inhibitors, UV blockers or absorbers, water scavengers and colorants. Surface active agents, including anionic, cationic, non-ionic and ampholytic surface active agents, can also be included in these formulations.

In some embodiments, a topical formulation (particularly a pour-on or spot-on formulation) comprises a carrier that promotes the absorption or penetration of the isoxazoline through the skin into the blood stream, other bodily fluids (lymph), and/or body tissue (fat tissue). Contemplated examples of dermal penetration enhancers include, for example, dimethylsulfoxide, isopropyl myristate, dipropylene glycol pelargonate, silicone oil, aliphatic esters, triglycerides, and fatty alcohols.

Topical localized formulations also (or alternatively) may comprise, for example, one or more spreading agents. These substances act as carriers that assist in distributing an active ingredient over the animal recipient's coat or skin. They may include, for example, isopropyl myristate, dipropylene glycol pelargonate, silicone oils, fatty acid esters, triglycerides, and/or fatty alcohols.

Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the formulation comprises a spreading agent, it also may be advantageous to include a dispersant, such as, for example, pyrrolidin-2-one, N-alkylpyrrolidin-2-one, acetone, polyethylene glycol, or an ether or ester thereof, propylene glycol, or synthetic triglycerides.

Optionally a crystallization inhibitor can be present selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

The formulation can also comprise an antioxidizing agent intended to inhibit oxidation in air. Particularly preferred antioxidizing agents are those conventional in the art and include, for example, butylated hydroxyanisole, butylated hydroxytoluene, ascorbic acid, sodium metabisulphite, propyl gallate, sodium thiosulphate or a mixture of them.

Suitable exemplary polymers ("polymeric agents") for gelling and/or adhering that may be used in the compositions of the invention include, but are not limited to, colloidal silicone dioxide, ethyl cellulose, methyl cellulose, methacrylic esters copolymers, carboxylated vinyl acetate, and polyvinylpropylene (PVP)/Vinyl acetate copolymers, Poloxamer 124, Poloxamer 188, Polybutene, Povidone K17 and Povidone K90.

The additional ingredients discussed above are well known to the practitioner in this art and may be obtained commercially or through known techniques.

The topical localized formulation is applied as a low volume of about 0.01 to 1 ml per kg, preferably about 0.05 to 0.1 ml per kg, with a total volume from 0.3 to 100 ml per animal, preferably limited to a maximum of about 50 ml depending on the target species.

For small companion animals such as dogs and cats the volume applied can be of the order of about 0.3 to about 6 ml, preferably of the order of about 0.4 to 2.0 ml per dose, for cats and of the order of about 0.4 to about 5 ml for dogs, depending on the weight of the animal.

An exemplary composition for topical administration to warm-blooded animals typically comprises, on a weight to volume basis, about 1%-50% w/v of an isoxazoline compound of formula I; about 5 to 25% w/v of N,N-diethyl-3-methylbenzamide; about 5% to 95% v/v of a co-solvent or solvent mixture, such as DMSO by itself or in combination with about 10 to 20% v/v of acetone, and/or about 10 to 20% v/v of a second cosolvent.

An exemplary composition for topical administration to warm-blooded animals typically comprises, on a weight to volume basis, about 1%-50% w/v of an isoxazoline compound of formula I; about 5 to 25% w/v of N,N-diethyl-3-methylbenzamide; about 5% to 95% v/v of a co-solvent or solvent mixture, such as N-methylpyrrolidone by itself or in combination with about 10 to 50% v/v of acetone, and/or about 10 to 20% w/v of a cosolvent.

An exemplary composition for topical administration to warm-blooded animals typically comprises, on a weight to volume basis, about 1%-50% w/v of an isoxazoline compound of formula I; about 5 to 25% w/v of N,N-diethyl-3-methylbenzamide; about 5% to 95% v/v of a co-solvent or solvent mixture, such as DMA by itself or in combination with about 10 to 50% v/v of acetone, and/or about 10 to 20% v/v of a cosolvent.

An exemplary composition for topical administration to warm-blooded animals typically comprises, on a weight to volume basis, about 1%-50% w/v of an isoxazoline compound of formula I; about 5 to 25% v/v of N,N-diethyl-3-methylbenzamide; about 5% to 95% v/v of a co-solvent or solvent mixture, such as DMA by itself or in combination with about 10 to 50% v/v of DMSO, and/or about 10 to 20% v/v of a cosolvent.

An exemplary composition for topical administration to warm-blooded animals typically comprises, on a weight to volume basis, about 1%-50% w/v of an isoxazoline compound of formula I; about 5 to 25% w/v of N,N-diethyl-3-methylbenzamide; about 5% to 95% v/v of a co-solvent or solvent mixture, such as DMSO by itself or in combination with about 10 to 50% v/v of Propylene glycol methyl ether, and/or about 10 to 20% v/v of a cosolvent.

An exemplary composition for topical administration to warm-blooded animals typically comprises, on a weight to volume basis, about 1%-50% w/v of an isoxazoline compound of formula I; about 5 to 25% w/v of N,N-diethyl-3-methylbenzamide; about 5% to 95% v/v of a co-solvent or solvent mixture, such as DMA or DMSO by itself or in combination with about 10 to 50% v/v of methyl ethyl ketone, and/or about 10 to 20% w/v of a cosolvent.

In one embodiment of the invention the topical localized formulation comprise at least one isoxazoline compound of formula I and a macrocyclic lactone compound of the avermectin or milbemycin class of compounds. Macrocyclic lactone compounds are either natural products or are semi-synthetic derivatives thereof. The structure of at least certain macrocyclic lactone compounds are closely related, e.g., by sharing a complex 16-membered macrocyclic lactone ring.

One compound for use within the scope of the present invention is ivermectin. Another macrocyclic lactone is moxidectin. Moxidectin, also known as LL-F28249 alpha, is known from U.S. Pat. No. 4,916,154. Another macocyclic lactone is selamectin. Selamectin is 25-cyclohexyl-25-de(1-methylpropyl)-5-deoxy-22,23-dihydro-5-(hydroxyimino)-avermectin B1 monosaccharide. Another preferred compound is milbemycin, especially milbemycin oxime. Milbemycin, or B41, is a substance which is isolated from the fermentation broth of a milbemycin-producing strain of *Streptomyces*. The microorganism, the fermentation conditions and the isolation procedures are described in U.S. Pat. Nos. 3,950,360 and 3,984,564.

Emamectin (4"-deoxy-4"-epi-methylaminoavermectin B1), which can be prepared as described in U.S. Pat. Nos. 5,288,710 and 5,399,717, is a mixture of two homologues, 4"-deoxy-4"-epi-methylaminoavermectin Bla and 4"-deoxy-4"-epi-methylaminoavermectin B1. Preferably, a salt of emamectin is used. Eprinomectin is chemically known as 4"-epi-acetylamino-4"-deoxy-avermectin B1.

For Latidectin, information can be found at "International Nonproprietary Names for Pharmaceutical Substances (INN) ". World Health Organization (WHO) Drug Information, vol. 17, no. 4, page 278-279, (2003).

Lepimectin is (6R,13R,25R)-5-O-demethyl-28-deoxy-6,28-epoxy-13-[(Z)-[(methoxyimino)phenylacetyl]oxy]-25-methylmilbemycin B mixture with (6R,13R,25R)-5-O-demethyl-28-deoxy-6,28-epoxy-25-ethyl-13-[(Z)-[(methoxyimino)phenylacetyl]oxy]milbemycin B.

Most especially preferred are topical localized formulations, wherein the composition comprises) 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (Compound A) and) moxidectin; or compound A; and selamectin, or Compound A and milbemycin, or Compound A and eprinomectin.

The macrocyclic lactone compounds are well known to a person skilled in the art and are easily obtained either commercially or through techniques known in the art.

The effective amount of the macrocyclic lactone compound is preferably between about 0.001 mg/kg bodyweight, preferentially about 0.005 to 10 mg/kg. The proportions, by weight, of the isoxazoline compound of formula (I) and of the macrocyclic lactone compound are preferably between about 5/1 and about 1/0.0001.

Other biologically active compounds useful in the formulations of the present invention can be selected from Insect Growth Regulators (IGRs) such as e.g. fenoxycarb, lufenuron, diflubenzuron, novaluron, triflumuron, fluazuron, cyromazine, methoprene, pyriproxyfen etc., thereby providing both initial and sustained control of parasites (at all stages of insect development, including eggs) on the animal subject, as well as within the environment of the animal subject.

Most especially preferred are topical localized formulations, wherein the composition comprises Compound A; and diflubenzuron or Compound A and methoprene, or Compound A; and pyriproxyfen, or Compound A and fenoxycarb, or Compound A; and fluazuron.

The effective amount of the IGR compound is preferably between about 0.1 mg/kg bodyweight, preferably about 1 mg, and about 10 mg. The proportions, by weight, of the isoxazoline compound of formula (I) and of the IGR compound are preferably between about 5/1 and about 0.000/1.

One aspect of the current invention is a method for permanently combating a parasite in an environment in which the animal is subjected to strong parasitic pressure where the administration of the topical localized formulation at a frequency far below a daily administration. For example, it is preferable for the treatment according to the invention to be carried out monthly, every 2 months, 3 months, 4 months, 5 months or 6 months especially on dogs, cats or ruminants (e.g. cattle or sheep).

The time period between treatments depends upon factors such as the parasite(s) being treated, the degree of infestation, the type of mammal or bird and the environment where it resides. It is well within the skill level of the practitioner to determine a specific administration period for a particular situation.

In some embodiments of this invention, the topical localized formulation of an isoxazoline of Formula (I) is administered to treat parasitoses of an animal (or make a medicament to treat parasitoses of an animal). The term "parasitoses" includes pathologic conditions and diseases associated with or caused by one or more ectoparasites directly, such as, for example, anemia and flea allergy dermatitis. It also includes pathologic conditions or diseases associated with caused by one or more vector-transmitted pathogens, such as, for example, Lyme disease, Ehrlichiosis (particularly Canine Ehrlichiosis), and Rocky Mountain spotted fever from vector ticks. The phrase "treatment of parasitoses" means to partially or completely inhibit the development of parasitoses of an animal susceptible to parasitoses, reduce or completely eliminate the symptoms of parasitoses of an animal having parasitoses, and/or partially or completely cure parasitoses of an animal having parasitoses. In general, the treatment of parasitoses is achieved by administering the formulation according to the invention comprising an isoxazoline of Formula (I) to control an ectoparasite infestation.

This invention also relates to treatment methods wherein at least an ancillary goal of controlling ectoparasites in and/or on an animal is to control an ectoparasitic infestation in an environment that is occupied (periodically or continuously) by the animal. In some such embodiments, for example, the animal is a companion animal (e.g., a cat or dog). The environment may be, for example, a house or other shelter; a room; a pen, a stall, or other confinement means; bedding; etc.

The topical localized formulations of the present invention are especially suitable for combating parasites that infest mammals (including humans). Mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Of particular note is the embodiment wherein the animals to be protected are domesticated dogs (i.e. *Canis lupus familiaris*) and domestic house cats (i.e. *Felis catus*).

Examples of invertebrate parasitic pests controlled by administering the topical localized formulation of this invention to an animal to be protected include ectoparasites (arthropods, acarines, etc) and endoparasites (helminths, e.g., nematodes, trematodes, cestodes, acanthocephalans, etc.).

In particular, the formulations of this invention are effective against ectoparasites including: flies such as *Haematobia*

(*Lyperosia*) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

This invention also is directed to kits that are, for example, suitable for use in performing the treatment methods described above. In general, such a kit will comprise a topical localized formulation according to the invention comprising a therapeutically effective amount of a isoxazoline of Formula (I), and an additional component(s). The additional component(s) may be, for example, one or more of the following: a diagnostic tool, instructions for administering the composition, an apparatus for administering the composition, a container comprising an excipient or other active ingredient to be mixed or administered in combination with the composition, or a memory aid (e.g., a stamp to adhere to a calendar to remind an animal owner of a time to administer a subsequent dose of the composition).

As used in the specification and claims, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study, and can be readily appreciated by one of ordinary skill in the art.

As used herein, the term "w/w" designates weight/weight, the term "w/v" designates weight/volume, and the term "mg/kg" designates milligrams per kilogram of body weight.

Example 1

Preparation of Formulations According to the Invention

Composition C

The calculated amount of e.g. 7 grams of 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (Compound A), were weighted and filled into a flask. The required volume of excipients was added, e.g. 8 mL of DMA and 6.25 mL of DMSO. Compound A was dissolved under mild stirring or shaking. This solution was brought to a final volume of 25 mL with ethyl lactate.

Using essentially the same procedure described hereinabove for composition C, composition A-V of table 2 and the formulations of table 3 were prepared. An alternative approach to the preparation was to weigh-in the excipients. The required weight was calculated based on the density of each product. Or, the order of addition was changed, e.g. excipients were blended and Compound A was introduced at a later stage.

Physicochemical parameters, that indicate the suitability of the formulations for topical localized (e.g. spot-on) administration, were evaluated. Compositions A to V of table 2 were tested using the following procedures Viscosity: The newtonian viscosity (q) was determined by means of a rotational viscometer in a double gap cup and rotor system at 20° C.

Evaporation: The evaporation was determined in a weight-recording balance. The sample pan was heated to 50° C. over 4 h and weight loss was recorded.

Spreading diameter: The spreading diameter was determined by measuring the diameter of three 20 µL spots of test product on a sheet of plastic.

Water absorption: The water absorption was determined by determining the water concentration of a test product in contact with the surrounding atmosphere at a temperature of 25° C. after one day. In addition, the physical state of the test product, e.g. whether it was a clear solution, was also recorded.

Solubility: A saturated solution, i.e. a solution of a test compound in contact with undissolved particles of the test compound, was prepared and continuously shaken, temperature was recorded. The content of the compound in the solvent phase was determined by HPLC after approximately 24 h. The content result was taken as solubility. In some cases, the content was determined again after 48 h and the lower of the two results was taken as solubility.

Compatibility: Binary mixtures of the test compound and excipients were prepared and stored under defined storage conditions, e.g. 40° C., 75% RH. At study start and after defined storage periods, samples were analyzed for appearance, content and degradation products.

The physicochemical parameters of the formulations of Table 2 are summarized in Table 2a.

The results in Table 2a and the in vivo experiments where the formulations were administered to dogs show that the tested formulations are suitable for localized topical administration of isoxazoline compounds to animals.

Comparative Example 2

Spot-on formulations with conventional topical localized formulations and isoxazoline compound solvents that were suggested e.g. in WO 2009/024541 were prepared and the solubility was tested in vitro as indicator for their suitability as formulations for localized topical administration of isoxazoline compounds to animals.

The details of the tested formulations are outlined in Table 4a (Comparative examples (1-7).

Compound A was not soluble in compare formulations 1, 2 and 3 at room temperature and 5° C.

Crystals/precipitations were detected in compare formulations 4 and 5a after leaving the formulations for some time exposed to the surrounding atmosphere.

Example 3

In Vivo Trials—Spot-on Administration of the Formulations to Dogs

The formulations of Table 2 were administered as spot-on to dogs at an 4-[5-(3,5-Dichlorophenyl)-5-trifluoromethyl-4,5-dihydroisoxazol-3-yl]-2-methyl-N-[(2,2,2-trifluoro-ethyl-carbamoyl)-methyl]-benzamide (Compound A) dosis of 25 mg/kg bodyweight. Dogs were observed for local and systemic tolerance of the treatment and the cosmetic appearance of the administration site was evaluated.

Plasma samples were taken of all dogs pre-administration and 2, 4, 8 hours after administration, on Day, D1, D3, D7 and, D14 and subsequently weekly until D56. The plasma was analyzed for Compound A by HPLC-MS/MS.

Results: The mean concentration of compound A in dog plasma is shown in FIGS. 1 to 6.

No local or systemic adverse reactions were observed. The cosmetic appearance was acceptable for the formulations, as only minor effects on appearance were detected for a short duration.

Example 4

In Vivo Trials—Formulation Comprising Compound A and Moxidectin Spot-on Administration to Dogs Formulation N of Table 2 was administered as spot-on to dogs at a Compound A dosage of 25 mg/kg bodyweight and moxidectin dosage of 2.5 mg/kg bodyweight. Dogs were observed for local and systemic tolerance of the treatment and the cosmetic appearance of the administration site was evaluated. Plasma samples were taken of all dogs pre-administration 2, 4, 8 hours after administration, on Day 0, D1, D3, D7 and D14 and subsequently weekly until D56. The plasma was analyzed for Compound A and moxidectin concentration.

Results: The mean plasma concentration of the compound A and moxidectin in dogs is shown in FIG. 7.

No local or systemic adverse reactions were observed. The cosmetic appearance was acceptable.

Example 5

Evaluation of the Efficacy of Test Formulations Against Ticks in Dogs

In this evaluation, Beagle dogs of mixed sex, were used and assigned to treatment and control groups. On day D-2, each dog was infested with 50 unfed adult ticks, *Rhipicephalus sanguineus* (*R. sanguineus*).

The dogs received on Day 0 the treatments (formulations indicated in table 1) at a dosage of 25 mg/kg body weight of the Compound A. The formulations were administered using a pipette. The dose was applied as a line at the dorsal neck at the base of the skull.

One Group was left untreated. The dogs were observed for any immediate reactions to the treatments, and were observed for post-treatment adverse reactions, skin irritation, and behavior of test formulations at the time of treatment, after approximately 2, 4 and 8 hours, and on Days 1, 2 and 7 following administration of the treatments. Thereafter, dogs were observed once daily for the remainder of the study.

All ticks were removed 48 hours after treatment. Removed ticks were assessed according to the following categories: Efficacy No: for—live free, live attached—live engorged/not engorged, and dead—engorged, Efficacy Yes: For dead, free, dead attached not engorged.

Tick counts were transformed and geometric means were used to calculate percent efficacy for the treatments. The results are shown in Table 1.

TABLE 1

Result of in vivo efficacy studies

| Formulation No. | Study characteristics | Tick efficacy after 2 days [geometric mean, %] |
|---|---|---|
| C | *R. sanguineus*, 6 dogs, notional control groups | 88.5-94.5 |
| H | *R. sanguineus*, 6 dogs, notional control groups | 91.8-96.1 |
| J | *R. sanguineus*, 4 dogs, notional control groups | 81.6-91.1 |
| L | *R. sanguineus*, 4 dogs, notional control groups | 45.7-73.9 |
| M | *R. sanguineus*, 4 dogs, notional control groups | 98.4-99.2 |
| N | *R. sanguineus*, 4 dogs, notional control groups | 96.5-98.3 |
| R | *R. sanguineus*, 4 dogs, notional control groups | 98.4-99.2 |

Example 6

Assessment for Cosmetic Effects after Topical Administration in a Variety of Dog Breeds and Coat Lengths and Characteristics Test formulations C and H of Table 2 were evaluated.

The study was conducted using 40 mixed sex adult dogs (n=20 per formulation) with a range of body weights and ages. The formulation was administered as a topical line-on directly to the skin between the shoulder blades and the lumbosacral region. The length of the line was determined by the dosing volume.

The application site and the hair coat was observed closely for spreading of the formulations and for determining if any of the spot-on solution ran off the animal during and directly after administration. Furthermore the application site was observed for signs of residues and wetness at 8, 24, 48 and 96 hours after administration. In addition to observations of the application site appearance, the overall appearance of the dogs' coat was assessed, particularly the hair in the proximity of the administration site for signs such as dryness, wiry look, brittleness, dullness, hair loss and the appearance of residue and the smell of hair and skin.

The skin was assessed for signs of local irritation. Furthermore dogs were observed for systemic tolerance For each time point each assessment parameter was scored (compared to the pre-administration score on D0) as 0=no change, 1=slight change, 2=moderate change or 3=severe change.

Results: The scoring is summarized in Tables A to D.

The formulations were easy to apply and did not emanate any noticeable odor. The drying time after application was fast for both formulations Formulation C displayed a propensity to form some powdery residues in the hair of 10 dogs at 8 hour assessment. As for the overall appearance at 24 hours, the application site was not noticeable on 17 dogs for Formulation C and on 15 dogs for Formulation H.

TABLE A

Group 1 Formulation C Wetness post application

| Time post application | Number of dogs with each score reduced | | | |
|---|---|---|---|---|
| | 3 (wet) | 2 (greasy) | 1 (slightly greasy) | 0 (dry) |
| 8 hours | 0 | 3 | 4 | 13 |
| 24 hours | 0 | 0 | 0. | 20 |
| 48 hours | 0 | 0 | 0 | 20 |
| 96 hours | 0 | 0 | 0 | 20 |

TABLE B

Group 1 Formulation C Residues post application

| Time post application | Number of dogs with each score reduced | | | |
|---|---|---|---|---|
| | 3 (severe) | 2 (moderate) | 1 (slight) | 0 (no change) |
| 8 hours | 4 | 1 | 5 | 10 |
| 24 hours | 2 | 5 | 3 | 10 |
| 48 hours | 0 | 7 | 2 | 11 |
| 96 hours | 1 | 4 | 5 | 10 |

TABLE C

Group 2 Formulation H Wetness post application

| Time post application | Number of dogs with each score reduced | | | |
|---|---|---|---|---|
| | 3 (wet) | 2 (greasy) | 1 (slightly greasy) | 0 (dry) |
| 8 hours | 0 | 2 | 8 | 10 |
| 24 hours | 0 | 0 | 2 | 18 |
| 48 hours | 0 | 0 | 0 | 20 |
| 96 hours | 0 | 0 | 0 | 20 |

TABLE D

Group 2 Formulation H Residues post application

| Time post application | Number of dogs with each score reduced | | | |
|---|---|---|---|---|
| | 3 (severe) | 2 (moderate) | 1 (slight) | 0 (no change) |
| 8 hours | 0 | 0 | 0 | 20 |
| 24 hours | 0 | 3 | 2 | 15 |
| 48 hours | 0 | 1 | 4 | 15 |
| 96 hours | 0 | 1 | 3 | 16 |

Example 7

Assessment for Cosmetic Effects after Topical Administration in a Variety of Dog Breeds and Coat Lengths and Characteristics Formulation N of Table 2 was evaluated.

The study was conducted using 38 mixed sex adult dogs with a range of body weights and ages. The formulation was administered as a topical line-on directly to the skin between the shoulder blades and the lumbosacral region. The length of the line was determined by the dosing volume.

The application site and the hair coat was observed closely for spreading of the formulations and for determining if any of the spot-on solution ran off the animal during and directly after administration. Furthermore the application site was observed for signs of residues and wetness at 8, 24, 48 and 96 hours after administration. In addition to observations of the application site appearance, the overall appearance of the dogs' coat was assessed, particularly the hair in the proximity of the administration site for signs such as dryness, wiry look, brittleness, dullness, hair loss and the appearance of residue and the smell of hair and skin.

The skin was assessed for signs of local irritation. Furthermore dogs were observed for systemic tolerance For each time point each assessment parameter was scored (compared to the pre-administration score on D0) as 0=no change, 1=slight change, 2=moderate change or 3=severe change.

Results: Summarized scoring is shown in Table E and F.

The formulation N was easy to apply and did not emanate any noticeable odor. The drying time after application was fast. As for the overall appearance at 24 hours, the application site was visible on 13 dogs but not noticeable on the remaining 25 dogs.

TABLE E

Wetness post application

| Time post application | Number of dogs with each score reduced | | | |
|---|---|---|---|---|
| | 3 (wet) | 2 (greasy) | 1 (slightly greasy) | 0 (dry) |
| 8 hours | 2 | 11 | 12 | 13 |
| 24 hours | 0 | 4 | 8 | 26 |
| 48 hours | 0 | 1 | 4 | 33 |
| 96 hours | 0 | 0 | 1 | 37 |

TABLE F

Residues post application

| Time post application | Number of dogs with each score reduced | | | |
|---|---|---|---|---|
| | 3 (severe) | 2 (moderate) | 1 (slight) | 0 (no change) |
| 8 hours | 0 | 0 | 0 | 38 |
| 24 hours | 0 | 0 | 2 | 36 |
| 48 hours | 0 | 2 | 5 | 31 |
| 96 hours | 0 | 1 | 2 | 35 |

Comparative Example 8

Spot-on formulations with conventional topical localized formulations and isoxazoline compound solvents that were suggested e.g. in WO2009/024541 were prepared. Such formulations were administered as spot-on to dogs to evaluate their cosmetic appearance after localized topical administration to animals.

The details of the tested formulations are outlined in Table 4b.

Crystals/precipitations were detected after administration of compare formulations 5b, 6 and 7 after some hours on the majority of the dogs under assessment. Other observations regarding the cosmetic appearance were a certain stickiness of the hair coat at the administration site and a noticeable wetness in a smaller portion of the dogs.

TABLE 2

Formulations of Compound A, Excipient: Amount [ml or mg]

| Formulation No. | active (mg) | DEET (mL) | Acetone (mL) | DMSO (mL) | DMA (mL) | Ethyl Lactate (mL) | Ethanol (mL) | Eucalyptol (mL) | Glycofurol (mL) | Methyl ethyl ketone (mL) | Povidone (mg) |
|---|---|---|---|---|---|---|---|---|---|---|---|
| A | 280 | 0.11 | 0.41 |  | 0.36 |  |  |  | 0.20 |  |  |
| B | 250 | 0.18 | 0.15 |  | 0.50 |  |  |  |  |  |  |
| C | 280 | 0.15 |  | 0.25 | 0.32 | 0.09 |  |  |  |  |  |
| D | 250 | 0.23 |  | 0.10 | 0.35 |  | 0.15 |  |  |  |  |
| E | 280 | 0.14 | 0.14 |  | 0.36 |  |  |  | 0.17 |  |  |
| F | 250 | 0.10 | 0.20 | 0.25 | 0.18 |  |  | 0.05 |  |  | 20 |
| G | 250 | 0.23 |  |  | 0.40 |  |  |  |  | 0.20 |  |
| H | 280 | 0.10 |  |  | 0.35 | 0.16 |  |  | 0.20 |  |  |
| I | 250 | 0.17 | 0.15 | 0.10 | 0.4 |  |  |  |  |  |  |
| J | 250 | 0.15 | 0.07 | 0.25 | 0.35 |  |  |  |  |  |  |
| K | 280 | 0.17 | 0.14 |  | 0.35 |  |  |  | 0.15 |  |  |
| L | 400 | 0.15 | 0.27 |  | 0.30 |  |  |  |  |  |  |
| M | 333 | 0.20 | 0.17 |  | 0.40 |  |  |  |  |  |  |
| N | 250 | 0.10 | 0.18 |  | 0.35 |  |  |  | 0.20 |  |  |
| O | 250 | 0.18 |  | 0.25 |  |  |  |  |  |  | 0.40 |
| P | 280 | 0.10 | 0.16 |  | 0.35 |  |  |  | 0.20 |  |  |
| Q | 300 | 0.44 |  | 0.35 |  |  |  |  |  |  |  |
| R | 250 | 0.18 | 0.10 | 0.25 | 0.30 |  |  |  |  |  |  |
| S | 280 | 0.14 | 0.10 |  | 0.36 | 0.04 |  |  | 0.17 |  |  |
| T | 250 | 0.15 |  | 0.25 | 0.35 | 0.07 |  |  |  |  |  |
| U | 250 | 0.18 | 0.30 | 0.25 |  |  |  |  | 0.10 |  |  |
| V | 250 | 0.10 | 0.22 |  | 0.5 |  |  |  |  |  |  |

TABLE 2a

Physicochemical parameters of formulations

| Formulation No. | Solubility [mg/mL] | Viscosity [mPas] | Evaporation [%] | Spreading [mm] | Water absorption after 1 d [appearance, %] |
|---|---|---|---|---|---|
| A |  | 9.44 | 35.05 |  |  |
| B | 679.3 | 3.69 | 47.81 | 24.13 | Clear, 25.74 |
| C | 719.4 | 7.64 | 34.46 | 21.06 | Clear, 40.27 |
| D | 623.2 | 4.41 | 42.16 | 26.44 | Clear, 48.44 |
| E |  | 8.63 | 34.91 |  |  |
| F | 754.7 | 19.86 | 39.33 | 14.50 | Turbid, 41.35 |
| G | 658.9 | 3.79 | 44.12 | 23.81 | Clear, 41.33 |
| H | 601.7 | 13.51 | 36.26 | 22.21 | Clear, 34.73 |
| I | 728.3 | 3.65 | 47.03 | 28.1 | Clear, 38.16 |
| J | 767.27 | 4.96 | 42.39 | 13.11 | Clear, 45.35 |
| K |  | 6.82 | 34.72 |  |  |
| L | 627.8 | 7.25 | 38.05 | 18.52 | Clear, 42.55 |
| M | 602.1 | 5.35 | 38.28 | 23.68 | Clear, 50.36 |
| N | 611.5 | 5.72 | 35.58 | 18.88 | Clear, 39.22 |
| O | 499.1 | 8.17 | 40.36 | 31.47 | Turbid, 51.67 |
| P | 617.2 | 5.79 | 35.72 | 19.76 | Clear, 29.84 |
| Q |  | 32.92 | 20.11 | 11.63 | Not determined, 32.81 |
| R | 685.6 | 5.41 | 37.26 | 11.26 | Clear, 47.34 |
| S |  | 8.09 | 32.82 |  |  |
| T | 706.10 | 6.48 | 38.79 | 16.80 | Clear, 43.28 |
| U | 637.8 | 4.10 | 40.24 | 16.75 | Clear, 48.48 |
| V | 721.7 | 2.60 | 56.12 | 33.1 | Clear, 38.81 |

TABLE 3

Formulations of Compound A, Excipient: Amount [ml or mg] (utv = until total volume)

| active [mg] | DEET | Acetone [mL] | DMA [mL] | DMSO [mL] | Glycofurol [mL] | Cyclohexanone [mL] | Diethylene glycol monoethyl ether [mL] | NMP [mL] | Dimethyl isosorbide | Ethyl L-lactate [mL] | Methyl ethylketone [mL] | Eucalyptol [mL] |
|---|---|---|---|---|---|---|---|---|---|---|---|---|
| 250 | 0.15 | utv |  | 0.05 |  | 0.1 |  |  |  | 0.1 |  |  |
| 250 | 0.1 | utv |  | 0.25 |  | 0.1 |  |  |  | 0.1 |  |  |
| 250 | 0.1 | utv |  |  |  |  | 0.1 |  | 0.05 |  | 0.2 |  |
| 250 | 0.1 | utv |  |  |  |  | 0.2 |  | 0.05 |  |  |  |
| 250 | 0.1 |  |  |  |  |  |  | 0.1 | 0.05 |  | utv |  |
| 250 | 0.15 | utv |  |  |  |  |  | 0.15 |  |  |  | 0.05 |
| 250 | utv | 0.35 |  |  |  |  |  | 0.2 |  |  |  | 0.05 |
| 300 | utv |  | 0.3 | 0.2 |  |  |  | 0.2 |  |  |  |  |
| 250 | utv | 0.25 |  |  |  |  |  | 0.25 |  |  |  | 0.05 |
| 250 | utv |  |  |  |  |  |  | 0.25 |  |  | 0.3 |  |
| 250 | utv | 0.3 |  |  |  |  |  | 0.25 |  |  |  |  |
| 300 | utv | 0.25 |  |  |  |  |  | 0.35 |  |  |  |  |
| 250 | 0.15 | utv |  | 0.05 |  |  |  |  | 0.05 | 0.2 |  |  |
| 250 | 0.15 |  | 0.3 |  |  |  |  |  | 0.05 |  | utv |  |
| 250 | 0.2 | utv |  |  |  |  |  |  | 0.05 |  |  |  |

TABLE 3-continued

Formulations of Compound A, Excipient: Amount [ml or mg] (utv = until total volume)

| 250 | 0.2  |     | utv  | 0.1  |     |     | 0.05 |      | utv |
|-----|------|-----|------|------|-----|-----|------|------|-----|
| 250 | 0.15 | utv |      | 0.1  |     |     | 0.1  |      |     |
| 250 | 0.15 | utv |      | 0.05 |     |     | 0.1  | 0.15 |     |
| 250 | utv  |     |      | 0.2  |     |     | 0.1  |      | 0.3 |
| 250 | utv  |     | 0.3  |      |     |     | 0.1  |      | 0.2 |
| 300 | utv  | 0.25|      | 0.35 |     |     |      |      |     |
| 280 | 0.14 | utv | 0.36 |      | 0.17|     |      | 0.04 |     |

| active [mg] | DEET | Acetone [mL] | DMA [mL] | DMSO [mL] | Glycofurol [mL] | Ethyl L-lactate [mL] | Methyl ethyl ketone [mL] | Eucalyptol [mL] |
|---|---|---|---|---|---|---|---|---|
| 250 | 0.2  | utv  |      | 0.1  |     | 0.1  |     | 0.1 |
| 250 | 0.2  |      | utv  | 0.1  |     | 0.1  |     |     |
| 250 | 0.2  | utv  |      | 0.05 |     | 0.1  |     |     |
| 250 | 0.17 | utv  |      | 0.05 |     | 0.1  |     |     |
| 250 | utv  |      | 0.35 | 0.1  |     | 0.15 |     |     |
| 250 | utv  |      | 0.35 | 0.1  |     | 0.15 |     |     |
| 250 | 0.2  |      | utv  | 0.1  |     | 0.2  |     |     |
| 250 | 0.15 |      | utv  | 0.25 |     | 0.2  |     |     |
| 250 | 0.15 |      | utv  | 0.25 |     | 0.25 |     |     |
| 250 | 0.2  |      | utv  | 0.1  |     | 0.3  |     |     |
| 250 | 0.2  |      | 0.4  |      |     | utv  |     |     |
| 250 | 0.2  |      | 0.3  |      |     | utv  |     |     |
| 250 | 0.15 |      | 0.35 | 0.25 |     | utv  |     |     |
| 280 | 0.1  |      | 0.35 |      | 0.2 | utv  |     |     |
| 280 | 0.1  | 0.12 | 0.35 |      | 0.2 | utv  |     |     |
| 280 | 0.1  | 0.08 | 0.35 |      | 0.2 | utv  |     |     |
| 280 | 0.1  | 0.04 | 0.35 |      | 0.2 | utv  |     |     |
| 280 | 0.15 |      | 0.35 | 0.22 |     | utv  |     |     |
| 280 | 0.15 |      | 0.32 | 0.25 |     | utv  |     |     |

| active [mg] | DEET | Acetone [mL] | DMA [mL] | DMSO [mL] | MEK [mL] | Eucalyptol [mL] | gamma Hexalactone [mL] | Isopropyl alcohol [mL] | L Menthol [mg] | Limonene [mL] |
|---|---|---|---|---|---|---|---|---|---|---|
| 250 | utv  | 0.35 |     | 0.25 | 0.05 |     |      |     |     |     |
| 250 | 0.1  | 0.2  | utv | 0.25 | 0.05 |     |      |     |     |     |
| 250 | utv  | 0.2  |     | 0.25 | 0.1  |     |      |     |     |     |
| 250 | utv  | 0.3  |     | 0.25 | 0.1  |     | 0.15 |     |     |     |
| 250 | utv  | 0.3  |     | 0.2  |      |     | 0.2  |     |     |     |
| 250 | utv  | 0.25 |     | 0.2  |      |     | 0.2  |     |     |     |
| 300 | utv  |      |     | 0.35 |      |     |      | 0.3 |     |     |
| 250 | utv  |      |     | 0.25 |      |     |      |     | 100 |     |
| 333 | 0.17 | utv  | 0.32|      |      |     |      |     | 100 |     |
| 400 | 0.17 | utv  | 0.25|      |      |     |      |     | 100 |     |
| 250 | 0.17 | utv  | 0.4 |      |      |     |      |     |     | utv |
| 250 | 0.15 |      | 0.3 |      |      |     |      |     |     | utv |
| 250 | 0.2  |      | 0.3 |      |      |     |      |     |     | utv |
| 400 | 0.15 |      | 0.3 |      |      |     |      |     |     | utv |
| 250 | 0.15 |      |     | 0.35 |      |     |      |     |     |     |
| 300 | utv  |      |     | 0.35 |      | 0.2 |      |     |     |     |
| 250 | utv  |      | 0.4 |      |      | 0.2 |      |     |     |     |
| 250 | 0.15 |      | utv |      |      | 0.2 |      |     |     |     |
| 250 | utv  |      |     | 0.25 |      | 0.3 |      |     |     |     |
| 300 | utv  | 0.35 |     | 0.25 |      |     |      |     |     |     |

| active [mg] | DEET | Acetone [mL] | DMA [mL] | DMSO [mL] | Methyl ethyl ketone [mL] | Eucalyptol [mL] | Povidone K90 [mg] | gamma Nonalactone [mL] |
|---|---|---|---|---|---|---|---|---|
| 250 | 0.2  | utv  |     | 0.1  |     |      |    | 0.2 |
| 250 | utv  | 0.35 |     | 0.3  |     |      |    |     |
| 250 | 0.1  | 0.2  | utv | 0.25 |     | 0.05 | 20 |     |
| 250 | utv  | 0.35 |     | 0.25 |     |      | 50 |     |
| 250 | utv  | 0.35 |     | 0.25 |     |      | 10 |     |
| 250 | utv  | 0.35 |     | 0.25 |     |      | 15 |     |
| 250 | utv  | 0.35 |     | 0.25 |     |      |    |     |
| 250 | utv  | 0.35 |     | 0.25 |     |      |    |     |
| 250 | 0.1  | utv  |     | 0.1  |     |      |    |     |
| 250 | 0.2  | utv  | 0.4 |      |     |      |    |     |
| 250 | 0.2  | utv  | 0.25|      |     |      |    |     |
| 250 | 0.15 | utv  |     | 0.35 |     |      |    |     |
| 300 | utv  | 0.1  | 0.35|      |     |      |    |     |
| 300 | utv  | 0.1  | 0.5 |      |     |      |    |     |
| 250 | utv  | 0.15 | 0.5 |      |     |      |    |     |
| 250 | 0.1  | utv  | 0.5 |      |     |      |    |     |
| 250 | utv  | 0.15 | 0.4 | 0.1  |     |      |    |     |

TABLE 3-continued

Formulations of Compound A, Excipient: Amount [ml or mg] (utv = until total volume)

| active [mg] | DEET | Acetone [mL] | DMA [mL] | DMSO [mL] | Glycofurol [mL] | Propylene glycol methyl ether [mL] | Povidone K17 [mg] | Polybutene [mg] | Poloxamer 124 [mL] | Nerol [mL] |
|---|---|---|---|---|---|---|---|---|---|---|
| 250 | utv | 0.1 | 0.5 | | | | | | | 0.05 |
| 250 | utv | 0.35 | | 0.25 | | | | | 0.05 | |
| 250 | 0.2 | utv | 0.4 | | | | | 10 | | |
| 250 | utv | 0.35 | | 0.25 | | | 50 | | | |
| 250 | 0.2 | utv | 0.4 | | | | | | | |
| 300 | 0.2 | utv | 0.4 | | | | | | | |
| 300 | 0.2 | utv | 0.3 | | | | | | | |
| 300 | 0.17 | utv | 0.3 | | | | | | | |
| 250 | 0.15 | utv | 0.35 | 0.25 | | | | | | |
| 300 | utv | 0.2 | | 0.35 | | | | | | |
| 300 | utv | | 0.2 | 0.35 | | | | | | |
| 250 | utv | | 0.5 | 0.1 | | | | | | |
| 250 | utv | | | 0.25 | | 0.3 | | | | |
| 250 | utv | | | 0.25 | | 0.4 | | | | |
| 250 | utv | 0.3 | | 0.2 | | | | | | |
| 250 | 0.05 | utv | 0.4 | | 0.2 | | | | | |
| 250 | 0.1 | utv | 0.35 | | 0.2 | | | | | |
| 250 | 0.15 | utv | 0.25 | 0.35 | | | | | | |
| 250 | 0.18 | utv | 0.2 | 0.35 | | | | | | |
| 250 | 0.18 | utv | 0.25 | 0.3 | | | | | | |
| 250 | 0.18 | utv | 0.3 | 0.25 | | | | | | |
| 400 | 0.15 | utv | 0.44 | | | | | | | |

| active [mg] | DEET | Acetone [mL] | DMA [mL] | DMSO [mL] | Glycofurol [mL] | Propylene glycol methyl ether [mL] | Povidone K17 [mg] | Polybutene [mg] | Poloxamer 124 [mL] | Nerol [mL] |
|---|---|---|---|---|---|---|---|---|---|---|
| 400 | 0.15 | utv | 0.3 | | | | | | | |
| 333 | 0.2 | utv | 0.4 | | | | | | | |
| 280 | 0.1 | utv | 0.35 | | 0.2 | | | | | |
| 280 | 0.15 | utv | 0.42 | | 0.1 | | | | | |
| 280 | 0.17 | utv | 0.35 | | 0.15 | | | | | |
| 280 | 0.07 | utv | 0.4 | | 0.2 | | | | | |
| 280 | 0.15 | utv | 0.32 | | 0.2 | | | | | |
| 280 | 0.09 | utv | 0.38 | | 0.2 | | | | | |
| 280 | 0.11 | utv | 0.36 | | 0.2 | | | | | |
| 280 | 0.14 | utv | 0.36 | | 0.17 | | | | | |
| 10 | 0.17 | utv | 0.45 | | 0.21 | | | | | |
| 250 | 0.1 | utv | 0.35 | | 0.2 | | | | | |
| 300 | utv | | | 0.35 | | | | | | |
| 280 | 0.1 | utv | 0.35 | | 0.2 | | | | | |

TABLE 4a

Comparative examples in vitro tested

| Formulation No. | active (mg) | DEET (mL) | NMP (mL) | DMSO (mL) | Dipropylene glycol monomethyl ether (mL) | Ethyl Lactate (mL) | Propylene glycol (mL) | Isopropyl myristiate (mL) | Benzyl-alcohol (mL) |
|---|---|---|---|---|---|---|---|---|---|
| Compare 1 | 500 | | | 0.45 | utv | | | 0.10 | |
| Compare 2 | 500 | — | | 0.35 | | utv | 0.1 | | |
| Compare 3 | 500 | — | 0.3 | | utv | | | | |
| Compare 4 | 500 | — | | 0.35 | utv | | | | 0.075 |
| Compare 5a | 500 | | | 0.45 | utv | | | | |

TABLE 4b

Comparative examples in vivo tested

| Formulation No. | active (mg) | DEET (mL) | NMP (mL) | DMSO (mL) | Dipropylene glycol monomethyl ether (mL) | Benzyl-alcohol (mL) | Phenyl-ethyl-alcohol (mL) |
|---|---|---|---|---|---|---|---|
| Compare 5b | 500 | — | utv | | | | |
| Compare 6 | 500 | — | | 0.35 | | | utv |
| Compare 7 | 500 | — | | utv | | | |

What is claimed is:

1. A method for treatment of parasite infestation of an animal comprising spot-on or pour-on administration of a localized topical formulation comprising 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide and a veterinary acceptable liquid carrier vehicle wherein the liquid carrier vehicle comprises N,N-diethyl-3-methylbenzamide as a solvent, wherein the formulation has a cosmetically acceptable appearance after administration.

2. The method of claim 1 wherein the veterinary acceptable liquid carrier comprises a co-solvent of at least two of acetone, ethyl-L-lactate, dimethyl sulfoxide, dimethylacetamide and glycofurol.

3. The method of claim 1 wherein the topical localized formulation comprises additionally an effective amount of a macrocyclic lactone compound and/or an insect growth regulator compound.

4. The method of claim 3 wherein the macrocyclic lactone compound is selected from ivermectin, moxidectin, milbemycin, selamectin, emamectin, latidectin and lepimectin or a salt thereof and the insect growth regulator compound is selected from fenoxycarb, lufenuron, diflubenzuron, novaluron, triflumuron, fluazuron, cyromazine, methoprene and pyriproxyfen.

\* \* \* \* \*